US008137512B2

(12) United States Patent
Tanaka et al.

(10) Patent No.: US 8,137,512 B2
(45) Date of Patent: Mar. 20, 2012

(54) PROCESS FOR ANALYZING SAMPLE BY CAPILLARY ELECTROPHORESIS METHOD

(75) Inventors: Yoshihide Tanaka, Osaka (JP); Shinichi Wakida, Osaka (JP); Yusuke Nakayama, Kyoto (JP); Satoshi Yonehara, Kyoto (JP)

(73) Assignees: National Institute of Advanced Industrial Science and Technology, Tokyo (JP); Arkray, Inc., Kyoto (JP)

( * ) Notice: Subject to any disclaimer, the term of this patent is extended or adjusted under 35 U.S.C. 154(b) by 367 days.

(21) Appl. No.: 12/376,744

(22) PCT Filed: Aug. 29, 2007

(86) PCT No.: PCT/JP2007/066752
§ 371 (c)(1),
(2), (4) Date: Mar. 20, 2009

(87) PCT Pub. No.: WO2008/029685
PCT Pub. Date: Mar. 13, 2008

(65) Prior Publication Data
US 2010/0187110 A1 Jul. 29, 2010

(30) Foreign Application Priority Data
Sep. 4, 2006 (JP) .................................. 2006-239641

(51) Int. Cl.
*B01D 57/02* (2006.01)
*B01D 59/42* (2006.01)
*C02F 1/469* (2006.01)
*C07K 1/26* (2006.01)

(52) U.S. Cl. ..................................................... 204/251

(58) Field of Classification Search .................. 204/451, 204/601
See application file for complete search history.

(56) References Cited

U.S. PATENT DOCUMENTS

| | | | | |
|---|---|---|---|---|
| 5,292,416 A * | 3/1994 | Novotny et al. | ............... | 204/453 |
| 5,431,793 A | 7/1995 | Wang et al. | | |
| 5,611,903 A * | 3/1997 | Janssens et al. | ............... | 204/454 |
| 6,586,065 B1 | 7/2003 | Katayama et al. | ............ | 428/36.9 |
| 0,256,232 A1 | 12/2004 | Jiang et al. | | |
| 0,040,396 A1 | 2/2006 | Baba et al. | | |
| 2005/0163853 A1 * | 7/2005 | Szente et al. | ................ | 424/486 |
| 2005/0274616 A1 | 12/2005 | Frederic et al. | ............... | 204/451 |
| 2007/0017870 A1 * | 1/2007 | Belov et al. | ................... | 210/656 |
| 2009/0200166 A1 * | 8/2009 | Nakayama et al. | ........... | 204/451 |
| 2010/0006436 A1 * | 1/2010 | Oishi et al. | ................... | 204/451 |
| 2010/0032294 A1 * | 2/2010 | Nakayama et al. | ........... | 204/451 |
| 2010/0101953 A1 | 4/2010 | Yokoyama et al. | ........... | 204/601 |
| 2010/0155242 A1 * | 6/2010 | Nakayama et al. | ........... | 204/451 |
| 2010/0175996 A1 * | 7/2010 | Tanaka et al. | ................. | 204/451 |
| 2010/0258440 A1 * | 10/2010 | Sugiyama et al. | ............ | 204/451 |
| 2010/0282607 A1 * | 11/2010 | Oishi et al. | ................... | 204/450 |

FOREIGN PATENT DOCUMENTS

| | | |
|---|---|---|
| JP | 4-320957 | 11/1992 |
| JP | 5-503989 | 6/1993 |
| JP | 6-288984 | 10/1994 |
| JP | 8-094578 | 4/1996 |
| JP | 8-504037 | 4/1996 |
| JP | 9-105739 | 4/1997 |
| JP | H09-143202 | 6/1997 |
| JP | 9-510792 | 10/1997 |
| JP | H10-502175 | 2/1998 |
| JP | 10-505166 | 5/1998 |
| JP | H10-221305 | 8/1998 |
| JP | 2002-350413 | 12/2002 |
| JP | 3429709 B2 | 5/2003 |
| JP | 2004-286449 | 10/2004 |
| JP | 2005-249572 | 9/2005 |
| JP | 2005-291926 | 10/2005 |
| JP | 2005-326407 | 11/2005 |
| JP | 2006-016313 | 1/2006 |
| JP | 2006-145537 | 6/2006 |
| JP | 2008-170351 | 7/2008 |
| JP | 2008-164382 | 7/2009 |
| JP | 2008-170350 | 7/2009 |
| WO | WO 96/23220 | 8/1996 |
| WO | WO 2004/031757 | 4/2004 |
| WO | WO 2008/078781 | 7/2008 |

OTHER PUBLICATIONS

Kamiya, Masato et al. "Preparation of Ionic Polymer Coated Capillaries for Electrophoretic Analysis. 2", The Abstract of the 25th Symposium on Capillary Electrophoresis, The Division of Electrophoresis of the Japan Society for Analytical Chemistry, pp. 13-14, Nov. 15, 2005.

Doelman, Cees J.A. et al., "Capillary Electrophoresis System for Hemoglobin $A_{1c}$ Determinations Evaluated", Clinical Chemistry vol. 43, No. 4, pp. 644-648, 1997.

Sirén, Heli et al., "Direct Monitoring of Glycohemoglobin $A_{1c}$ in the Blood Samples of Diabetic Patients by Capillary Electrophoresis Comparison with an Immunoassay Method", Journal of Chromatography A, vol. 979, pp. 201-207, 2002.

(Continued)

*Primary Examiner* — Bruce Bell
(74) *Attorney, Agent, or Firm* — Morgan Lewis & Bockius LLP

(57) ABSTRACT

A process for analyzing a sample by a capillary electrophoresis method is provided that allows the apparatus to be reduced in size, allows a high analytical precision to be obtained, and can be carried out easily. The analytical process of the present invention is a process for analyzing a sample by a capillary electrophoresis method. The analytical process includes preparing a capillary tube to be used for the capillary electrophoresis method, and performing electrophoretic separation of a complex of a sample and an anionic group-containing compound that are bonded together, in the capillary tube, wherein the capillary tube includes an anionic layer that is formed of the anionic group-containing compound and that is coated on the inner wall of the capillary tube, and the anionic layer is fixed to the inner wall of the capillary tube by a covalent bond.

8 Claims, 6 Drawing Sheets

OTHER PUBLICATIONS

Y. Du et al., A novel polybrene/chondroitin sulfate C double coated capillary and its application in capillary electrophoresis, Chinese Journal of Chemistry, 2002, 20, 1557-1565.

Office Action of U.S. Appl. No. 12/376,739 dated Aug. 2, 2011.

Office Action issued Aug. 30, 2011 in corresponding Chinese Patent Application No. 200780029543.4 (English language translation included).

Office Action issued in a related U.S. Appl. No. 12/367,260, dated Sep. 15, 2011.

Office Action issued in a related U.S. Appl. No. 12/376,739, dated Sep. 14, 2011.

Timothy et al., "Capillaries Modified by Polyelectrolyte Multilayers for Electrophoretic Separations," Analytical Chemistry, 71(18):4007-4013 (1999).

Liu et al., "Poly(diallyldimethylammonium chloride) as a cationic coating for capillary electrophoresis," Journal of Chromatographic Science, 35(3): 126-130 (1997).

Office Action issued Oct. 21, 2011 in corresponding Chinese Patent Application No. 2007-80029192.7 (English language translation included).

Office Action issued in a related U.S. Appl. No. 12/367,260, dated Jan. 9, 2012.

\* cited by examiner

PROCESS FOR ANALYZING SAMPLE BY CAPILLARY ELECTROPHORESIS METHOD

The present application is a U.S. National Phase Application of International Application No. PCT/JP2007/066752, filed Aug. 29, 2007, which claims the benefit of Japanese Patent Application No. 2006-239641, filed Sep. 4, 2006, both of which are hereby incorporated by reference in their entirety.

TECHNICAL FIELD

The present invention relates to a process for analyzing a sample by a capillary electrophoresis method as well as a capillary tube and a capillary electrophoresis apparatus that are used for the process.

BACKGROUND ART

In the capillary electrophoresis method, ions that have gathered on the inner wall of a capillary tube are transferred upon voltage application to generate an electroosmotic flow, which transfers the sample, and thus electrophoresis is performed. For the capillary tube, one made of fused silica is used. In this case, however, adsorption of the sample may prevent a good electroosmotic flow from being obtained. Accordingly, techniques of coating the inner walls of capillary tubes have been proposed (Patent Documents 1, 2, 3, and 4). On the other hand, hemoglobin (Hb) in blood reacts with glucose in the blood to become glycated Hb. The glycated Hb in the blood reflects the past history of the blood glucose level in a biological body and therefore is considered as an index in, for example, diagnosis and treatment of diabetes. Particularly, glycated beta chain N-terminal valine is called hemoglobin A1c (HbA1c) and is measured by, for example, a laboratory test, as an especially important index. Examples of the method of measuring hemoglobin in blood include an agarose electrophoresis method, a capillary electrophoresis method, an HPLC method, an immunization method, an enzymatic method, etc. Among these, those allowing minute variations such as hemoglobin variants to be detected are the capillary electrophoresis method and the HPLC method. On the other hand, an apparatus for analyzing hemoglobin is required to be reduced in size. With respect to this point, it is difficult to reduce the size of the whole apparatus in the HPLC method. On the other hand, the capillary electrophoresis method allows the size of the whole apparatus to be reduced, with the apparatus being formed into a microchip.

However, there is a problem in that the aforementioned conventional capillary electrophoresis method does not allow hemoglobin to be analyzed with high precision. In order to solve this problem, there is a technique in which the inner wall of a capillary tube is coated with a protein, which then is coated with polysaccharide (Patent Document 5). However, in this technique, an operation is required in which the inner wall of a capillary tube is coated with a protein each time the analysis is carried out, and therefore there is a problem in that the analysis becomes complicated. On the other hand, there is a method in which capillary electrophoresis is carried out with a zwitterionic type of running buffer that is allowed to contain a flow inhibitor such as aliphatic diamine, with the inner wall of the capillary tube not being coated (Patent Document 6). However, there is a problem in that this method allows variant hemoglobin to be separated but does not allow hemoglobin A1c to be separated. These problems apply to the general capillary electrophoresis method with respect to not only hemoglobin but also other samples.

[Patent Document 1] JP 2005-291926 A
[Patent Document 2] JP 4(1992)-320957 A
[Patent Document 3] JP 5(1993)-503989 A
[Patent Document 4] JP 8(1996)-504037 A
[Patent Document 5] JP 9(1997)-105739 A
[Patent Document 6] JP 2006-145537 A

DISCLOSURE OF THE INVENTION

Accordingly, the present invention is intended to provide a process for analyzing a sample by a capillary electrophoresis method that allows the apparatus to be reduced in size, allows a high analytical precision to be obtained, and can be carried out easily as well as a capillary tube and a capillary electrophoresis apparatus that are used for the process.

In order to achieve the aforementioned object, an analytical process of the present invention is a process for analyzing a sample by a capillary electrophoresis method. The process includes a step of preparing a capillary tube to be used for the capillary electrophoresis method, and a step of electrophoresing a complex of a sample and an anionic group-containing compound that are bonded together, in the capillary tube, wherein the capillary tube includes an anionic layer that is formed of the anionic group-containing compound and that is coated on an inner wall of the capillary tube, and the anionic layer is fixed to the inner wall of the capillary tube by a covalent bond.

A capillary tube of the present invention is a capillary tube for capillary electrophoresis to be used for the analytical process of the present invention, wherein an anionic layer formed of an anionic group-containing compound is coated on an inner wall of the capillary tube, and the anionic layer is fixed to the inner wall of the capillary tube by a covalent bond.

A capillary electrophoresis apparatus of the present invention is a capillary electrophoresis apparatus to be used for the analytical process of the present invention, wherein the capillary tube of the present invention is included. The capillary electrophoresis apparatus of the present invention may be a microchip electrophoresis apparatus with a reduced size (formed into a microchip) as described later.

In the analytical process of the present invention, the use of a capillary tube including an anionic layer fixed to the inner wall of the capillary tube by a covalent bond can prevent, for example, a protein in a blood sample, such as hemoglobin, from being adsorbed by the inner wall of the capillary tube. This makes it possible to generate a good electroosmotic flow. Furthermore, in the analytical process of the present invention, since a complex is generated by bonding a sample and an anionic group-containing compound, which then is performed electrophoretic separation, a higher separation efficiency is obtained as compared to the case where the sample alone is performed electrophoretic separation. Thus, according to the analytical process of the present invention, a sample such as hemoglobin can be analyzed in a short time with high precision. Moreover, since the anionic layer is fixed firmly to the inner wall of the capillary tube, once it is formed, it is not separated therefrom easily, even when being washed, which allows it to be used repeatedly. Accordingly, in the analytical process of the present invention, once the anionic layer is formed, it is not necessary to form the anionic layer every time an analysis is carried out, and thereby the analysis can be carried out easily. Furthermore, in the present invention, since the capillary electrophoresis method is employed, it is possible to reduce the size of the analysis apparatus.

BRIEF DESCRIPTION OF THE DRAWINGS

FIG. 3(A) is a plan view of the capillary electrophoresis apparatus of this example, FIG. 3(B) is a sectional view taken on line I-I shown in FIG. 3(A). and FIG. 3(C) is a sectional view taken on line II-II shown in FIG. 3(A).

BEST MODE FOR CARRYING OUT THE INVENTION

Figure 1:
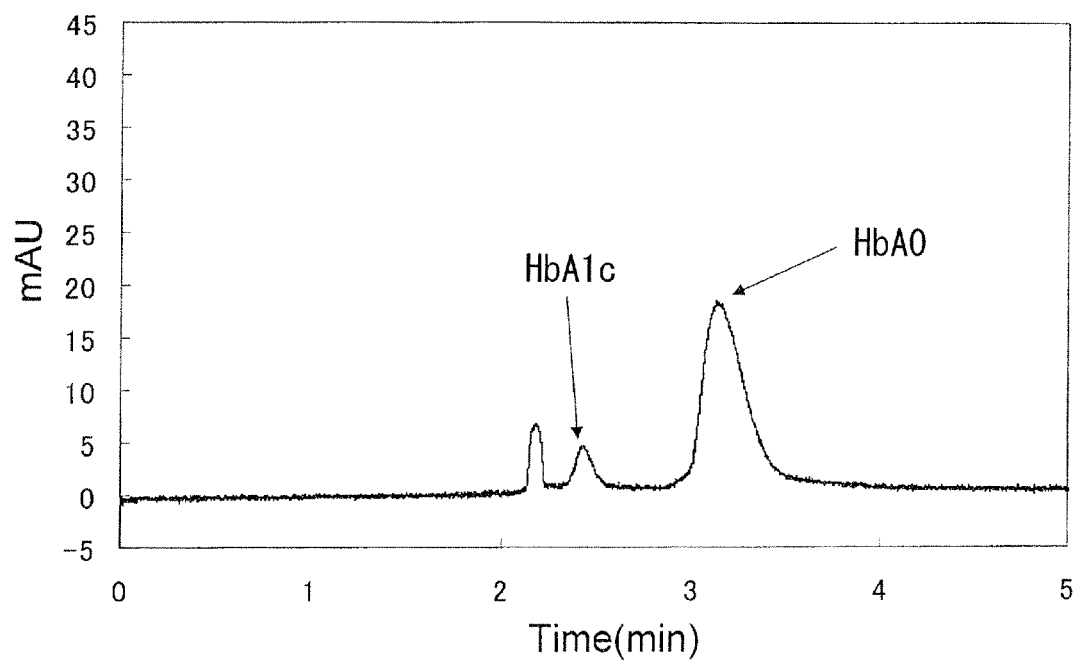
FIG. 1 is an electropherogram showing the result of analysis of hemoglobin in an example of the present invention.

In the present invention, the term "running buffer" denotes a buffer solution (buffer) that is used in an actual separation process. Preferably, in the capillary tube to be used in the analytical process of the present invention, a sample is introduced into a running buffer containing an anionic group-containing compound, and voltage then is applied across both ends of the capillary tube to perform electrophoretic separation of a complex of the sample and the anionic group-containing compound.

In the analytical process and the capillary tube of the present invention, a preferable anionic group-containing compound that forms the complex together with the sample is an anionic group-containing polysaccharide. Examples of the anionic group-containing polysaccharide include sulfated polysaccharide, carboxylated polysaccharide, sulfonated polysaccharide, and phosphorylated polysaccharide. Particularly, sulfated polysaccharide and carboxylated polysaccharide are preferable. The sulfated polysaccharide is preferably, for example, chondroitin sulfate or heparin, more preferably chondroitin sulfate. The carboxylated polysaccharide is preferably alginic acid or a salt thereof (for instance, sodium alginate). There are seven types of chondroitin sulfates A, B, C, D, E, H, and K and any of them may be used.

In the analytical process and the anionic group-containing compound that forms the anionic layer of the capillary tube of the present invention, the anionic group is preferably at least one of a sulfone group and a carboxyl group.

In the present invention, it is preferable that the sample contains hemoglobin.

The capillary electrophoresis apparatus of the present invention may include a substrate, a plurality of liquid reservoirs, and a capillary tube, wherein the plurality of liquid reservoirs may be formed in the substrate and may be allowed to communicate with one another through the capillary tube, and the capillary tube may be the capillary tube of the present invention. In this case, the substrate has a maximum length, for example, in the range of 10 to 100 mm, preferably in the range of 30 to 70 mm, a maximum width, for instance, in the range of 10 to 60 mm, and a maximum thickness, for example, in the range of 0.3 to 5 mm. The maximum length of the substrate is the length of the portion that is longest in the longitudinal direction of the substrate. The maximum width of the substrate is the length of the portion that is longest in the direction (width direction) perpendicular to the longitudinal direction of the substrate. The maximum thickness of the substrate is the length of the portion that is longest in the direction (thickness direction) perpendicular to both the longitudinal direction and the width direction of the substrate. As described above, the capillary electrophoresis apparatus of the present invention may be a microchip electrophoresis apparatus with a reduced size (formed into a microchip).

Next, the present invention is described in detail.

As described above, the capillary tube of the present invention is provided with an anionic layer formed on the inner wall thereof.

The material for the capillary tube is not particularly limited.

Examples thereof include glass, fused silica, and plastic. The inner wall of a capillary tube made of glass or fused silica usually has negative electric charges. The inner wall of a capillary tube made of plastic has positive or negative electric charges depending on the presence or absence and the type of the polar group contained in the plastic or is uncharged (nonpolar). Even in the case of plastic having no polar group, introduction of a polar group allows it to have electric charges. A commercial product may be used as the capillary tube made of plastic. Examples of the capillary tube include those formed of, for example, polymethylmethacrylate, polycarbonate, polystyrene, polyethylene, polytetrafluoroethylene (PTFE), and polyether ether ketone (PEEK). The inner diameter of the capillary tube is, for example, in the range of 10 to 200 μm, preferably in the range of 25 to 100 μm. The length of the capillary tube is, for example, in the range of 10 to 1000 mm.

For the formation of the anionic layer on the inner wall of the capillary tube with the anionic group-containing compound, for example, a compound containing the anionic group and a reactive group may be used. When the capillary tube is made of glass or fused silica, a compound containing an anionic group and silicon (a silylation agent) can be used. As described above, the anionic group is preferably at least one of a sulfone group and a carboxyl group.

Examples of the silylation agent include 2-(4-chlorosulfonylphenyl)ethyltrimethoxysilane, and 2-(4-chlorosulfonylphenyl)ethyltrichlorosilane.

For the silylation agent, one obtained by substituting the silicon atom with titanium or zirconium may be used. One silylation agent may be used alone or two or more of them may be used in combination.

The anionic layer is formed using the silylation agent, for example, as follows. First, a silylation agent is dissolved or dispersed in an organic solvent and thereby a treatment liquid is prepared. The organic solvent to be used for preparing the treatment liquid can be, for example, dichloromethane or toluene. The concentration of the silylation agent of the treatment liquid is not particularly limited. This treatment liquid is passed through a capillary tube made of glass or fused silica and is heated. This heating allows the silylation agent to be bonded to the inner wall of the capillary tube by a covalent bond. As a result, the anionic group is placed on the inner wall of the capillary tube. Thereafter, it is washed with at least one of an organic solvent (for instance, dichloromethane, methanol, or acetone), an acid solution (for example, phosphoric acid), an alkaline solution, and a surfactant solution (aftertreatment). Preferably, this washing is carried out, although it is optional. A commercial product may be used as the capillary tube having an anionic layer formed with the silylation agent.

The running buffer is not particularly limited, but a buffer containing acid used therein is preferred. Examples of the acid include maleic acid, tartaric acid, succinic acid, fumaric acid, phthalic acid, malonic acid, and malic acid. Preferably, the running buffer contains a weak base. Examples of the weak base include arginine, lysine, histidine, and tris. The running buffer has a pH, for example, in the range of 4.5 to 6. The types of the buffer of the running buffer include MES, ADA, ACES, BES, MOPS, TES, and HEPES. In the running buffer, the anionic group-containing compound that forms a complex together with the sample has a concentration, for example, in the range of 0.01 to 5 wt %.

The analytical process of the present invention can be carried out with respect to, for example, a sample containing hemoglobin as follows.

First, a capillary tube made of glass or fused silica is prepared. An anionic group-containing compound has been fixed to the inner wall of the capillary tube by a covalent bond. Distilled water is passed through the capillary tube and thereby it is washed. The time over which the distilled water is passed therethrough is, for example, 1 to 10 minutes, and the pressure applied when the distilled water is passed therethrough is, for example, 0.05 to 0.1 MPa. Subsequently, a running buffer containing an anionic group-containing polysaccharide such as chondroitin sulfate is passed through the capillary tube under pressure applied with, for example, a pump. The time over which it is passed therethrough is, for example, 10 to 60 minutes and the pressure applied when it is passed therethrough is, for example, 0.05 to 0.1 MPa. With the capillary tube being filled with the running buffer, a hemoglobin-containing sample is introduced into the capillary tube, and voltage then is applied across both the ends of the capillary tube to carry out electrophoresis. The hemoglobin-containing sample is not particularly limited and is, for example, a sample obtained by hemolyzing whole blood. This sample may be diluted with distilled water or a running buffer. The hemoglobin-containing sample is introduced from the anode side of the capillary tube. The hemoglobin thus introduced forms a complex by being bonded with the anionic group-containing polysaccharide contained in the running buffer. Voltage application generates an electroosmotic flow in the running buffer contained in the capillary tube and thereby the complex is transferred toward the cathode side of the capillary tube. The voltage applied is, for example, in the order of 10 to 30 kV. This transfer is detected by an optical method. The detection made by the optical method is not particularly limited. Preferably, it is carried out with a wavelength of 415 nm.

In the present invention, the hemoglobin to be analyzed is not particularly limited. Examples thereof include normal hemoglobin, glycated hemoglobin (for instance, HbA1c, labile HbA1c, and GHbLys), and hemoglobin variants. In the present invention, it is possible to separate HbA1c and hemoglobin other than that from each other to analyze them.

Next, the capillary electrophoresis apparatus of the present invention is described using examples. However, the capillary electrophoresis apparatus of the present invention is not limited to the following examples.

Figure 3:
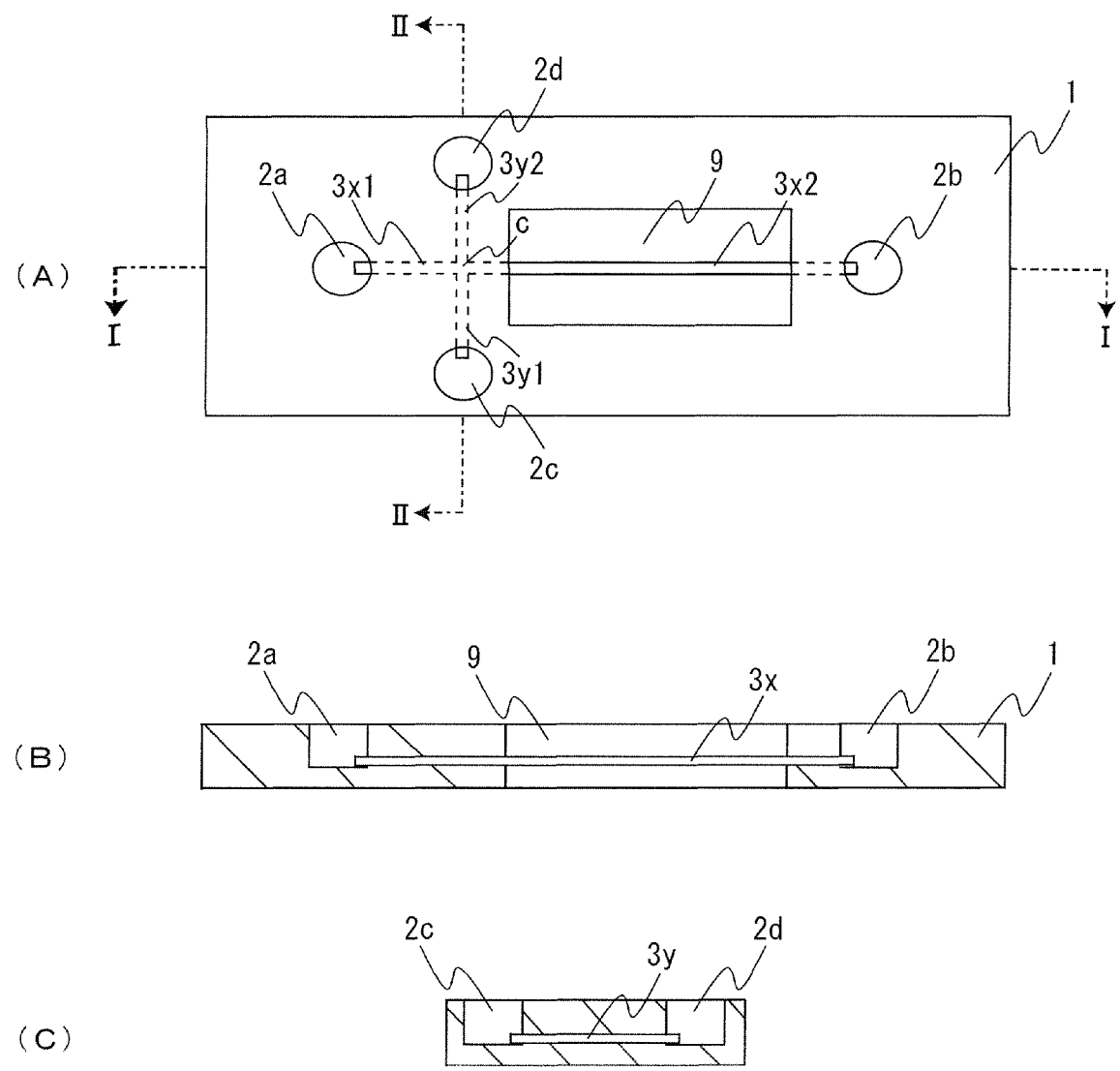
FIG. 3 shows diagrams illustrating the configuration of an example of the capillary electrophoresis apparatus of the present invention.

FIG. 3 shows an example of the capillary electrophoresis apparatus according to the present invention. FIG. 3(A) is a plan view of the capillary electrophoresis apparatus of this example, FIG. 3(B) is a sectional view taken on line I-I shown in FIG. 3(A), and FIG. 3(C) is a sectional view taken on line II-II shown in FIG. 3(A). In those figures, for ease of understanding, for example, the sizes and ratios of the respective components are different from actual ones. The capillary electrophoresis apparatus of this example is a microchip electrophoresis apparatus with a reduced size (formed into a microchip). As shown in the figures, this microchip electrophoresis apparatus includes a substrate 1, a plurality (four in this example) of liquid reservoirs 2a to 2d, and four capillary tubes 3x1, 3x2, 3y1, and 3y2. All of the four capillary tubes are capillary tubes of the present invention. The four liquid reservoirs 2a to 2d include a first introduction reservoir 2a, a first recovery reservoir 2b, a second introduction reservoir 2c, and a second recovery reservoir 2d. In the four capillary tubes, one ends thereof meet at the central portion c to be joined together in a cross shape. Accordingly, the four capillary tubes communicate with one another at their inner parts. The substrate 1 is provided with a cavity for inserting the four capillary tubes thereinto (not shown in the figures). The capillary tube 3x1 is inserted into the substrate 1 so that the other end thereof is located at the bottom surface of the first introduction reservoir 2a. The capillary tube 3x2 is inserted into the substrate 1 so that the other end thereof is located at the bottom surface of the first recovery reservoir 2b. The capillary tubes 3x1 and 3x2 form a capillary channel 3x for sample analysis. The capillary tube 3y1 is inserted into the substrate 1 so that the other end thereof is located at the bottom surface of the second introduction reservoir 2c. The capillary tube 3y2 is inserted into the substrate 1 so that the other end thereof is located at the bottom surface of the second recovery reservoir 2d. The capillary tubes 3y1 and 3y2 form a capillary channel 3y for sample introduction. The plurality of liquid reservoirs 2a to 2d each are formed as a concave part in the substrate 1. The substrate 1 has a rectangular parallelepiped opening (window) 9 on the first recovery reservoir 2b side with respect to the capillary channel 3y for sample introduction. The microchip electrophoresis apparatus of this example is rectangular parallelepiped. However, the present invention is not limited thereto. The microchip electrophoresis apparatus of the present invention may have any shape as long as it does not cause any problems in the electrophoresis measurement. The planar shape of the microchip electrophoresis apparatus of this example is rectangular. However, the present invention is not limited thereto. The planar shape of the microchip electrophoresis apparatus of the present invention may be, for example, square or another shape. In the microchip electrophoresis apparatus of this example, the capillary channel 3x for sample analysis is different in maximum length from the capillary channel 3y for sample introduction. However, the present invention is not limited thereto. In the microchip electrophoresis apparatus of the present invention, the maximum length of the capillary channel 3x for sample analysis may be identical to that of the capillary channel 3y for sample introduction. Similarly with respect to items other than those described above, the configuration of the microchip electrophoresis apparatus of the present invention is not limited to this example.

Next, the process for producing the microchip electrophoresis apparatus of this example is described. However, the microchip electrophoresis chip may be produced by a process other than the production process described below.

In the microchip electrophoresis apparatus of this example, the substrate 1 to be used can be one formed of, for example, a glass or polymer material. Examples of the glass material include synthetic silica glass, and borosilicate glass. Examples of the polymer material include polymethylmethacrylate (PMMA), cycloolefin polymer (COP), polycarbonate (PC), polydimethylsiloxane (PDMS), polystyrene (PS), and polylactic acid.

In the microchip electrophoresis apparatus of this example, the maximum length, maximum width, and maximum thickness of the substrate 1 are as described above.

The inner diameters of the four capillary tubes are the same as that of the capillary tube of the present invention. The capillary channel 3x for sample analysis and the capillary channel 3y for sample introduction each have a maximum length, for example, in the range of 0.5 to 15 cm. The respective lengths of the four capillary tubes are determined according to the maximum lengths of the capillary channel $3x$ for sample analysis and the capillary channel $3y$ for sample introduction.

The volumes of the plurality of liquid reservoirs $2a$ to $2d$ are not particularly limited. For example, each of them has a volume of 1 to 1000 mm$^3$, preferably in the range of 50 to 100 mm$^3$. In FIG. 3, the shapes of the plurality of liquid reservoirs $2a$ to $2d$ are cylindrical. However, the present invention is not limited thereto. In the microchip electrophoresis apparatus of the present invention, the shapes of the plurality of liquid reservoirs are not particularly limited as long as they do not cause any problems in introduction and recovery of the sample described later. For example, each of them may have an arbitrary shape, such as a quadrangular prism shape, a quadrangular pyramidal shape, a conical shape, or a shape formed by combining them. Furthermore, the volumes and shapes of the plurality of liquid reservoirs may be identical to or different from one another.

An example of the process of producing a microchip electrophoresis apparatus of this example is described below. However, the microchip electrophoresis apparatus may be produced by a process other than the production process described below.

First, the substrate 1 is produced. The methods of forming the four liquid reservoirs $2a$ to $2d$ and the opening (window) 9 in the substrate 1 are not particularly limited. For example, when the material used for the substrate 1 is the aforementioned glass, the formation method can be, for instance, ultrasonic machining. For example, when the material used for the substrate 1 is the aforementioned polymer material, the formation method can be, for instance, a cutting method or a molding method such as injection molding, cast molding, or press molding that employs a mold. The four liquid reservoirs $2a$ to $2d$ and the opening (window) 9 each may be formed independently or all of them may be formed simultaneously. When the four liquid reservoirs $2a$ to $2d$ and the opening (window) 9 each are formed independently, they may be formed in any order. It is preferable that all the four liquid reservoirs $2a$ to $2d$ and the opening (window) 9 be formed simultaneously by, for example, a method that employs a mold, since the number of the steps is smaller in this case.

Next, the four capillary tubes are inserted into the substrate 1. Thus, a microchip electrophoresis apparatus of this example can be obtained.

Figure 4:
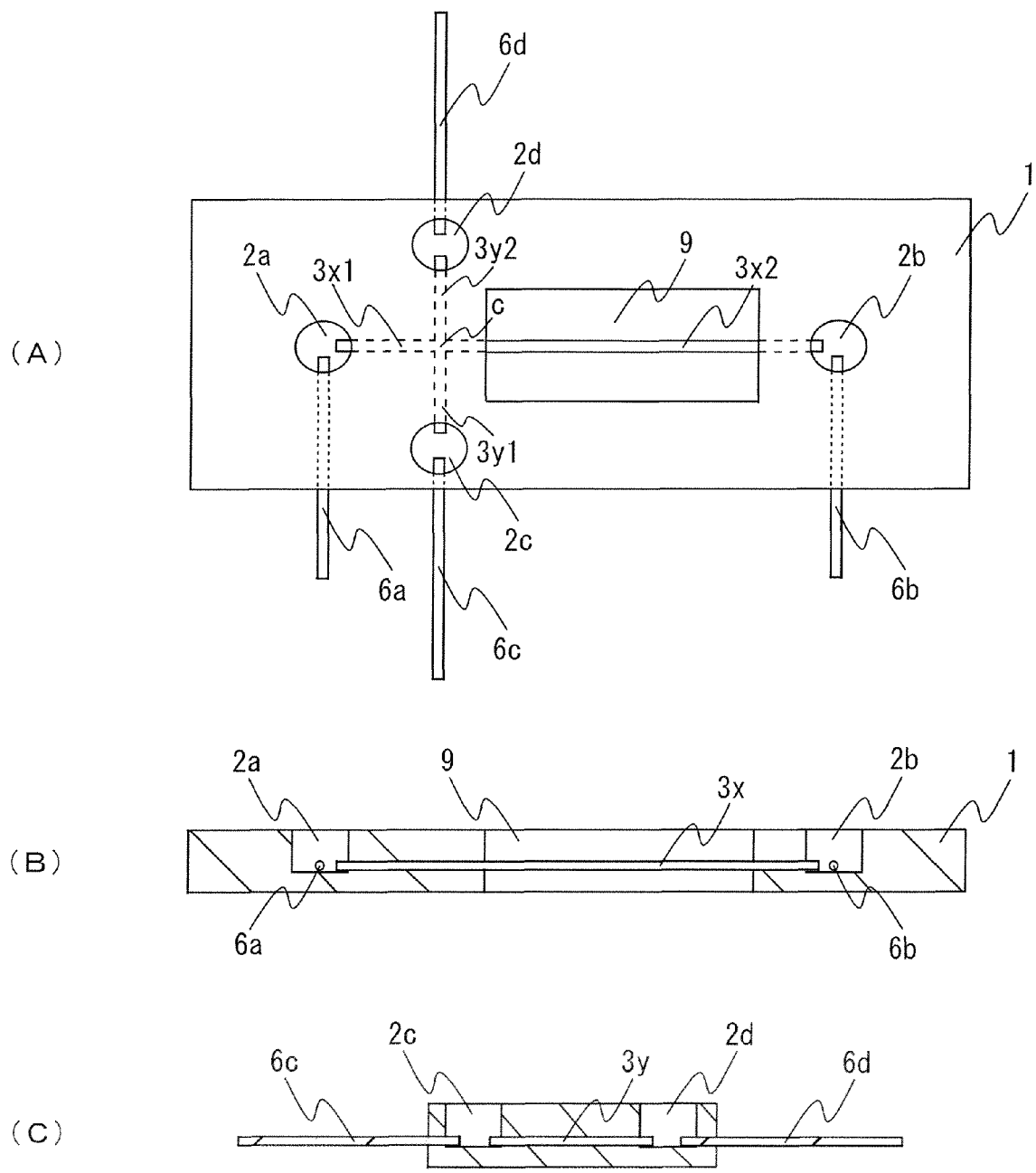
FIG. 4 shows diagrams illustrating the configuration of another example of the capillary electrophoresis apparatus of the present invention.

The microchip electrophoresis apparatus further may include a plurality of electrodes. FIG. 4 shows a microchip electrophoresis apparatus of this example that includes the plurality of electrodes. In FIG. 4, the identical parts to those shown in FIG. 3 are indicated with identical numerals and symbols. As shown in FIG. 4, this microchip electrophoresis apparatus has four electrodes $6a$ to $6d$. The four electrodes $6a$ to $6d$ are buried in the substrate 1 in such a manner that one ends thereof are located inside the plurality of liquid reservoirs $2a$ to $2d$, respectively. The four electrodes $6a$ to $6d$ can be disposed easily when, for example, holes for introducing the four electrodes $6a$ to $6d$ are formed in the side faces of the substrate 1 in producing the substrate 1. In the microchip electrophoresis apparatus, the plurality of electrodes are optional components. For example, the plurality of electrodes may be inserted into the plurality of liquid reservoirs when the microchip electrophoresis apparatus is used.

The plurality of electrodes $6a$ to $6d$ may be any electrodes, as long as they can be used for the electrophoresis method. The plurality of electrodes $6a$ to $6d$ each are, for example, an electrode made of stainless steel (SUS), a platinum (Pt) electrode, or a gold (Au) electrode.

The microchip electrophoresis apparatus further may include a pretreatment reservoir for hemolyzing a sample containing hemoglobin and diluting it. The treatment for hemolyzing the hemoglobin-containing sample is not particularly limited. For example, it may be a treatment for hemolyzing the hemoglobin-containing sample with a hemolytic agent. The hemolytic agent destroys, for example, a blood cell membrane of a blood cell component in the hemoglobin-containing sample. Examples of the hemolytic agent include the aforementioned running buffer, saponin, and "Triton X-100" (trade name) manufactured by Nacalai Tesque, Inc. Particularly preferable is the running buffer. Preferably, the pretreatment reservoir communicates with, for example, the introduction reservoirs. The pretreatment reservoir may be formed in a suitable place such as a place near the liquid reservoir with which it communicates, for example, the second introduction reservoir $2c$. When the pretreatment reservoir is provided, the hemoglobin-containing sample is introduced into the pretreatment reservoir. The hemoglobin-containing sample thus pretreated is introduced into a liquid reservoir that communicates with the pretreatment reservoir, for example, the second introduction reservoir $2c$ through the channel connecting the pretreatment reservoir and the second introduction reservoir $2c$. The pretreatment reservoir may have a configuration in which two reservoirs, a reservoir for hemolyzing the hemoglobin-containing sample and a reservoir for diluting the hemoglobin-containing sample, are in communication with each other.

Figure 5:
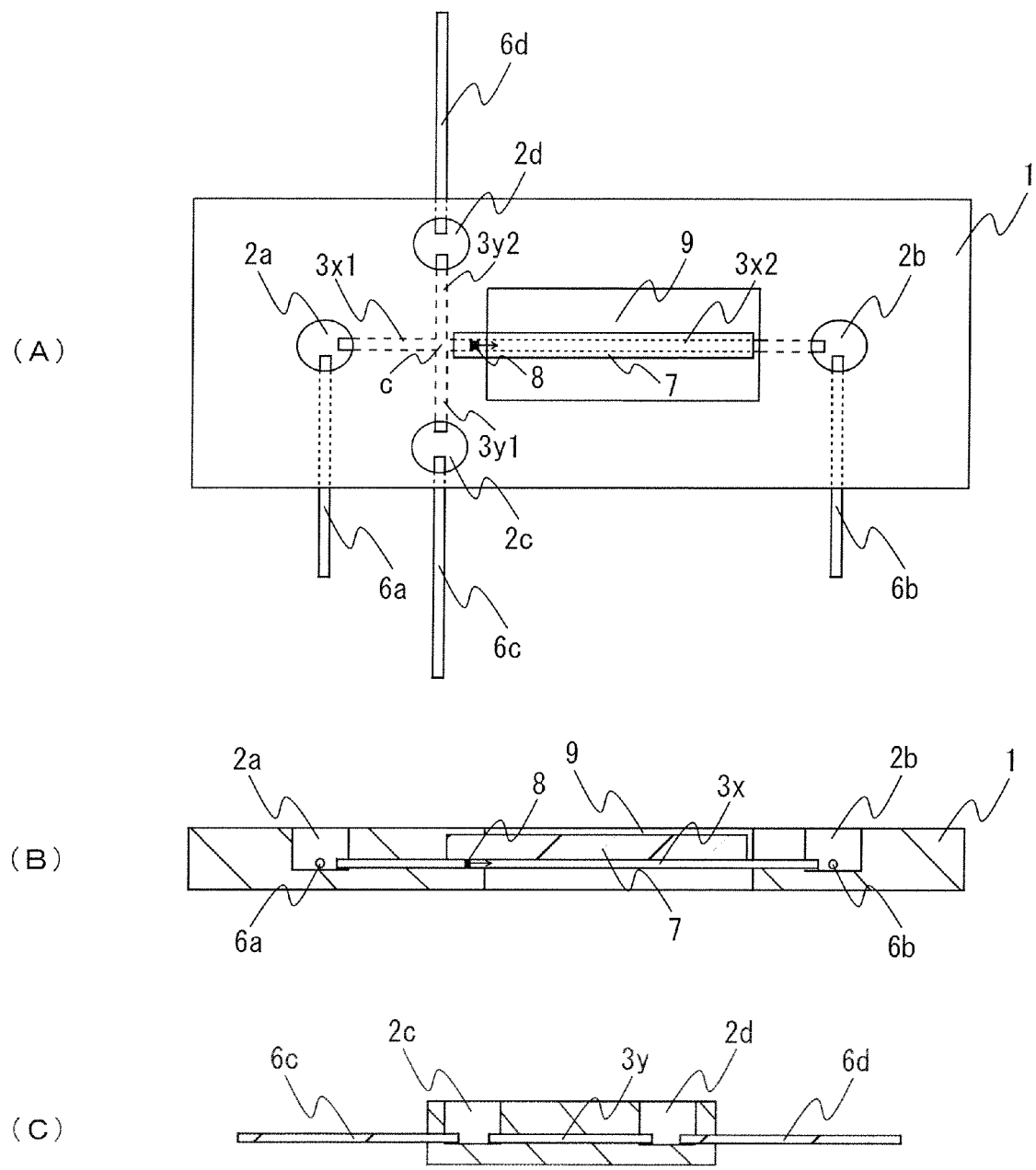
FIG. 5 shows diagrams illustrating the configuration of still another example of the capillary electrophoresis apparatus of the present invention.

The microchip electrophoresis apparatus further may include an analysis unit. FIG. 5 shows a microchip electrophoresis apparatus of this example including the analysis unit. In FIG. 5, identical parts to those shown in FIGS. 3 and 4 are indicated with identical numerals and symbols. As shown in FIG. 5, this microchip electrophoresis apparatus includes an analysis unit 7. In the microchip electrophoresis apparatus of this example, the analysis unit 7 is a detector (line detector). The line detector is disposed directly on the capillary tube $3x2$ in such a manner that it is located on the first recovery reservoir $2b$ side with respect to the intersection part between the capillary channel $3x$ for sample analysis and the capillary channel $3y$ for sample introduction. In this microchip electrophoresis apparatus, the substrate 1 is provided with a cavity into which the analysis unit (line detector) 7 is to be inserted, in addition to the cavity into which the four capillary tubes are to be inserted (not shown in the figures). The line detector has a light source and a detection unit built-in. The line detector emits light from the light source towards the sample to detect light reflected from the sample in the detection unit, and thereby measures absorbance. The analysis unit 7 is not limited to the line detector. It may be any analysis unit as long as, for example, it can analyze a sample containing hemoglobin. For example, the analysis unit 7 may be configured with a light source disposed under the microchip electrophoresis apparatus and a detection unit disposed in a place corresponding to the place where the line detector is disposed. In this case, light is emitted from the light source toward the sample, the transmitted light from the sample is detected in the detection unit, and thus absorbance is measured.

Figure 6:
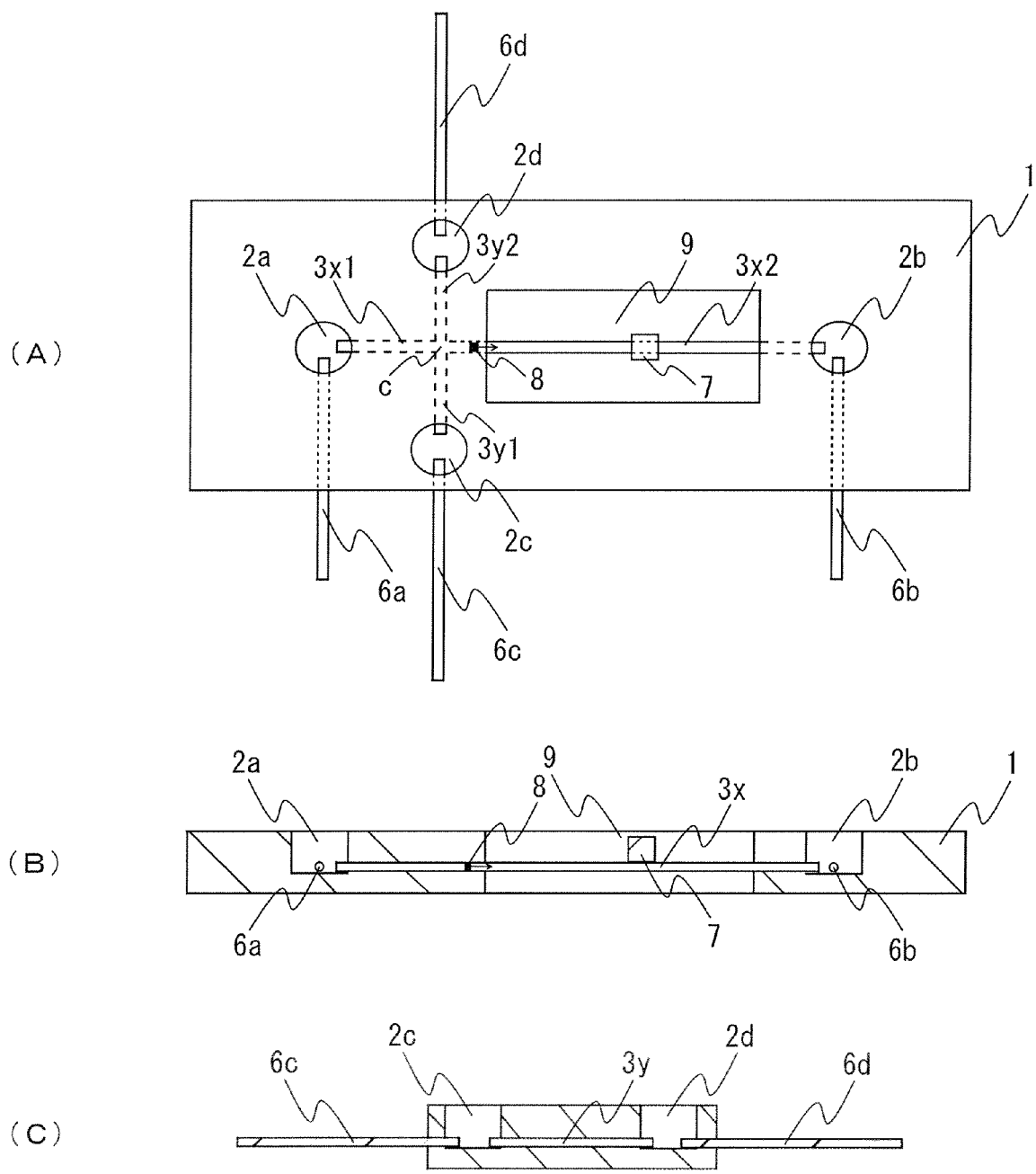
FIG. 6 shows diagrams illustrating the configuration of yet another example of the capillary electrophoresis apparatus of the present invention.

FIG. 6 shows still another example of the microchip electrophoresis apparatus according to the present invention. In FIG. 6, identical parts to those shown in FIG. 5 are indicated with identical numerals and symbols. As shown in FIG. 6, the microchip electrophoresis apparatus of this example has the same configuration as that of the microchip electrophoresis apparatus shown in FIG. 5 except that the analysis unit 7 is different. As in this example, the analysis unit 7 may measure the absorbance at one point.

The analytical processes of the present invention using the microchip electrophoresis apparatuses shown in FIGS. 5 and 6 can be carried out with respect to, for example, a sample containing hemoglobin, as follows.

First, distilled water is passed through the capillary channel 3x for sample analysis and the capillary channel 3y for sample introduction to wash them. The time over which the distilled water is passed therethrough and the pressure applied when it is passed therethrough are, for example, as described above. Subsequently, a running buffer containing an anionic group-containing polysaccharide such as chondroitin sulfate is passed through the capillary channel 3x for sample analysis and the capillary channel 3y for sample introduction under pressure applied with, for example, a pump. The time over which it is passed therethrough and the pressure thereof are, for example, as described above. Thereafter, the capillary channel 3x for sample analysis and the capillary channel 3y for sample introduction are filled with the running buffer by pressure or capillary action.

It is preferable that when the microchip electrophoresis apparatus is not in use (when no analysis is carried out), the step of filling them with the running buffer be completed beforehand, since it makes it possible to omit the respective steps described above and to proceed directly to the following step.

Subsequently, a hemoglobin-containing sample is introduced into the second introduction reservoir 2c. Examples of the hemoglobin-containing sample are as described above. When the microchip electrophoresis apparatus has the pretreatment reservoir (not shown in the figures), the hemoglobin-containing sample is introduced into the pretreatment reservoir and is pretreated there. Subsequently, voltage is applied to the electrode 6c and the electrode 6d to generate a potential difference between the ends of the capillary channel 3y for sample introduction. Thus, the hemoglobin-containing sample is introduced into the capillary channel 3y for sample introduction. The hemoglobin thus introduced is bonded with an anionic group-containing polysaccharide contained in the running buffer to form a complex. Voltage is applied to generate an electroosmotic flow in the running buffer contained in the capillary channel 3y for sample introduction and thereby the complex is transferred to the intersection part between the capillary channel 3x for sample analysis and the capillary channel 3y for sample introduction.

The potential difference between the electrode 6c and the electrode 6d is, for instance, in the range of 0.5 to 5 kV.

Next, voltage is applied to the electrode 6a and the electrode 6b to generate a potential difference between the ends of the capillary channel 3x for sample analysis. In this manner, the capillary channel having a potential difference between the ends thereof is changed momentarily from the capillary channel 3y for sample introduction to the capillary channel 3x for sample analysis, so that as shown with arrows in FIGS. 5 and 6, the sample 8 is transferred to the first recovery reservoir 2b side from the intersection part between the capillary channel 3x for sample analysis and the capillary channel 3y for sample introduction.

The potential difference between the electrode 6a and the electrode 6b is, for example, in the range of 0.5 to 5 kV.

Subsequently, the respective components of the hemoglobin-containing sample separated due to the difference in transfer rate are detected with the detector 7. Thus, the respective components of the hemoglobin-containing sample can be separated to be analyzed.

EXAMPLES

Next, examples of the present invention are described.

Example 1

A capillary tube (with an overall length of 32 cm, an effective length of 8.5 cm, and an inner diameter of 50 μm) made of fused silica was prepared. The capillary tube had an anionic layer formed with a silylation agent having a sulfone group that was fixed to the inner wall thereof by a covalent bond. Distilled water was passed through this capillary tube at a pressure of 0.1 MPa (1000 mbar) for 20 minutes to wash it. Subsequently, a running buffer (pH 5.5) was prepared that contains chondroitin sulfate added to 100 mM malic acid and an arginine acid aqueous solution at a ratio of 0.5 wt %. This running buffer was passed through the capillary tube at the same pressure as described above. With the capillary tube being filled with the running buffer, a sample containing hemoglobin dissolved in distilled water was injected into the capillary tube. Thereafter, a voltage of 10 kV was applied across both ends of the capillary tube, and thereby electrophoresis was carried out. The hemoglobin-containing sample was injected into the capillary tube from the anode side thereof. The hemoglobin that had been transferred was detected at an absorbance of 415 nm. This result is shown in the electropherogram in FIG. 1. As shown in FIG. 1, in this example, it was possible to detect normal hemoglobin (HbA0) and glycated hemoglobin (HbA1c) separately. Furthermore, the capillary tube used in this example allowed the analysis to be carried out immediately after being washed.

Example 2

Figure 2:
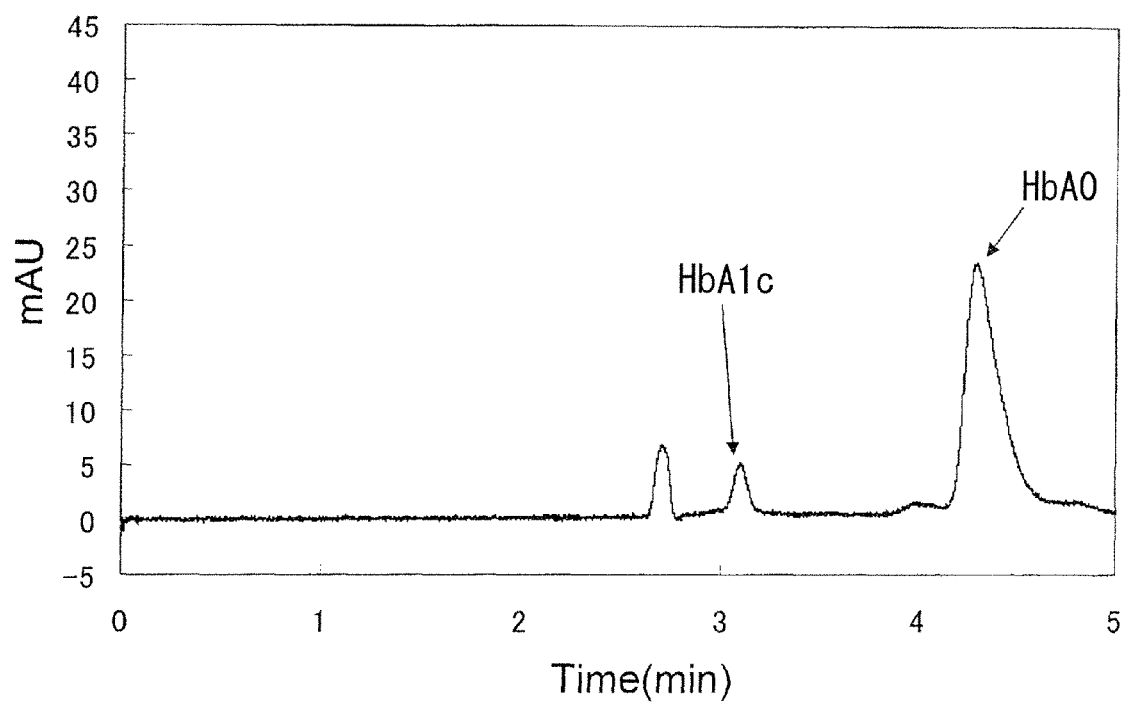
FIG. 2 is an electropherogram showing the result of analysis of hemoglobin in another example of the present invention.

Hemoglobin was analyzed by capillary electrophoresis carried out in the same manner as in Example 1 except that a capillary tube (with an overall length of 32 cm, an effective length of 8.5 cm, and an inner diameter of 50 μm) made of fused silica that had an anionic layer formed with a silylation agent having a carboxyl group that was fixed to the inner wall thereof by a covalent bond. This result is shown in the electropherogram in FIG. 2. As shown in FIG. 2, in this example, it was possible to detect normal hemoglobin (HbA0) and glycated hemoglobin (HbA1c) separately. Furthermore, the capillary tube used in this example allowed the analysis to be carried out immediately after being washed.

INDUSTRIAL APPLICABILITY

As described above, according to the present invention, a sample such as hemoglobin can be analyzed easily with high precision by the capillary electrophoresis method. Moreover, since the present invention employs the capillary electrophoresis method, it also is possible to reduce the size of the analysis apparatus. The present invention is applicable to all the fields where a sample such as hemoglobin is to be analyzed, such as laboratory tests, biochemical examinations, and medical research. The intended use thereof is not limited and it is applicable to a wide range of fields.

The invention claimed is:

1. A process for analyzing a sample by capillary electrophoresis comprising:
   preparing a capillary tube, and
   performing electrophoretic separation of a chemical complex comprising a component of the protein-containing sample and a first anionic group-containing compound, in the capillary tube, wherein the capillary tube has an inner wall coated with an anionic layer comprising a second anionic group-containing compound, and wherein the anionic layer is covalently bound to the inner wall.

2. The process of claim 1, wherein the capillary tube is prepared by introducing a running buffer containing the first anionic group-containing compound into the capillary tube to fill it, and applying the protein-containing sample to the filled capillary tube.

3. The process of claim 1, wherein the first anionic group-containing compound is an anionic group-containing polysaccharide.

4. The process of claim 3, wherein the anionic group-containing polysaccharide is at least one of a sulfated polysaccharide, a carboxylated polysaccharide, a sulfonated polysaccharide, and a phosphorylated polysaccharide.

5. The process of claim 4, wherein the sulfated polysaccharide is chondroitin sulfate.

6. The process of claim 1, wherein in the second anionic group-containing compound has at least one of a sulfone group and a carboxyl group.

7. The process of claim 1, wherein the protein-containing sample contains hemoglobin.

8. The process of claim 1, wherein the first anionic group-containing compound and the second anionic group-containing compound have the same chemical formula.

* * * * *